(12) United States Patent
Fujimoto et al.

(10) Patent No.: US 8,481,714 B2
(45) Date of Patent: Jul. 9, 2013

(54) LIGHT-RESPONSIVE ARTIFICIAL NUCLEOTIDE HAVING PHOTO-CROSSLINKING ABILITY

(75) Inventors: Kenzo Fujimoto, Nomi (JP); Yoshinaga Yoshimura, Nomi (JP); Shinya Toba, Toyama (JP); Yukari Nitta, Toyama (JP)

(73) Assignee: Japan Advanced Institute of Science and Technology, Nomi-shi (JP)

( * ) Notice: Subject to any disclaimer, the term of this patent is extended or adjusted under 35 U.S.C. 154(b) by 301 days.

(21) Appl. No.: 12/743,324

(22) PCT Filed: Nov. 19, 2008

(86) PCT No.: PCT/JP2008/003376
§ 371 (c)(1),
(2), (4) Date: May 17, 2010

(87) PCT Pub. No.: WO2009/066447
PCT Pub. Date: May 28, 2009

(65) Prior Publication Data
US 2010/0274000 A1   Oct. 28, 2010

(30) Foreign Application Priority Data
Nov. 19, 2007  (JP) ................................. 2007-299914

(51) Int. Cl.
*C07D 209/86* (2006.01)
*C07D 405/04* (2006.01)

(52) U.S. Cl.
USPC ........................................ 536/26.9; 536/28.6

(58) Field of Classification Search
USPC .............................................. 536/26.9, 28.6
See application file for complete search history.

(56) References Cited

U.S. PATENT DOCUMENTS
6,200,715 B1 *  3/2001  Fuller et al. .................. 430/59.6

FOREIGN PATENT DOCUMENTS
| | | |
|---|---|---|
| JP | 03-031850 A | 2/1991 |
| JP | 3753938 B2 | 3/2006 |
| JP | 3753942 B2 | 3/2006 |

OTHER PUBLICATIONS

Yoshimura et al, Organic Letters, 2008, 10(15), 3227-30.*
Notification of Transmittal of Translation of the International Preliminary Report on Patentability (Form PCT/IB/338) of International Application No. PCT/JP2008/003376 mailed Jul. 8, 2010 with Forms PCT/IPEA/409.
Canadian Office Action dated Aug. 26, 2011, issued in corresponding Canadian Patent Application No. 2,706,222.
LeClerc et al., "Heck, Direct Arylation, and Hydrogenation: Two or Three Sequential Reactions from a Single Catalyst", J. Org Chem., 2006, 71, pp. 1711-1714.; cited in Canadian Office Action dated Aug. 26, 2011, issued in corresponding Canadian Patent Application No. 2,706,222 and Supplementary European Search Report dated Nov. 21, 2011, issued in corresponding European Patent Application No. 08851080.
Supplementary European Search Report dated Nov. 21, 2011, issued in corresponding European Patent Application No. 08851080.5.
Ivan L. Baraznenok et al., "3-Trifloxy-3-trifluoromethylpropeniminium triflate: reaction with aromatic amines—an efficient synthesis of 2-trifluoromethylquinoline", Eur. J. Org. Chem. 1999, pp. 937-941.; cited in Supplementary European Search Report dated Nov. 21, 2011, issued in corresponding European Patent Application No. 08851080.
V.P. Lopatsinkii et al. "3-Vinyl-9-Alkylcarbazoles", Byul. Izobret.i Tovarnykh Znakov, 1963, vol. 23, p. 16: Chemical Abstracts, vol. 60, 1964, col. 11990b-c, the abstract No. 68158. Cited in ISR.
Tetsuya Aoyama et al. "Electro-Optic Effects in Mono- and Di-Substituted Carbazoles" MCLC S&T, Section B: Nonlinear Optics, 1996, 15(1-4), pp. 403-406. Cited in ISR.
L. Lin et al. "Photochemical Inactivation of Viruses and Bacteria in Platelet Concentrates by Use of a Novel Psoralen and Long-wavelength Ultraviolet Light" Transfusion, 1997, 37(4), pp. 423-435. Cited in ISR.
Yoshinaga Yoshimura et al. "Ultrafast Reversible Photo-Cross-linking Reaction:Toward in Situ DNA Manipulation", Organic Letters. 2008, 10(15), pp. 3227-3230, Cited in ISR.
International Search Report of PCTJP2008/003376, mailing date of Jan. 13, 2009.

* cited by examiner

*Primary Examiner* — Shaojia Anna Jiang
*Assistant Examiner* — Ganapathy Krishnan
(74) *Attorney, Agent, or Firm* — Westerman, Hattori, Daniels & Adrian, LLP

(57) ABSTRACT

The present invention provides a photoreactive crosslinking agent that is capable of crosslinking a sequence which cannot be photo-crosslinked by psoralen, and is capable of photo-crosslinking using a light having a longer wavelength, as compared with psoralen. The present invention also provides a compound having a group represented by formula (I) coupled with a group represented by formula (II).

11 Claims, 8 Drawing Sheets

LIGHT-RESPONSIVE ARTIFICIAL NUCLEOTIDE HAVING PHOTO-CROSSLINKING ABILITY

TECHNICAL FIELD

The present invention relates to a photoreactive crosslinking agent having a photoreactive nucleobase-like structure, which can be crosslinked with a nucleic acid compound, and a light-responsive artificial nucleotide having a photo-crosslinking ability, which has the nucleobase-like structure as a base moiety.

BACKGROUND ART

A fundamental technology employed in the field of molecular biology is coupling of nucleic acids. The coupling of nucleic acids is used, for example, in combination with hybridization, for the introduction of genes or detection of base sequences. Therefore, coupling of nucleic acids is an extremely important technology used not only in the basic research in molecular biology, but also in, for example, the diagnosis or treatment in the field of medicine, the development or production of therapeutic drugs, diagnostic drugs or the like, or the development or production of enzymes, microorganisms or the like in industrial and agricultural fields.

Coupling of nucleic acids has conventionally been carried out using, for example, DNA ligases and the like. However, reactions carried out by taking out such in vivo enzymatic reactions must be carried out under specially set conditions, and the reactions have disadvantages such as relatively high prices of the enzymes used and insufficient stability. In order to overcome such disadvantages, research has been conducted to find technologies for the coupling of nucleic acids which do not make use of enzymes.

As one such technology for the coupling of nucleic acids that does not use enzymes, there is an available method of using an organic compound which is capable of reacting with a nucleic acid. In recent years, technologies for the coupling of nucleic acids utilizing photoreaction are increasingly attracting attention because of their advantages such as that the temporal and spatial control of the reaction is freely achieved, and the reaction can be carried out under milder conditions as compared with general organic chemical reactions.

Among photocoupling technologies as such, those photocoupling technologies making use of 5-cyanovinyldeoxyuridine (Patent Document 1: Japanese Patent No. 3753938 and Patent Document 2: Japanese Patent No. 3753942) are known.

Another important technology similar to the coupling of nucleic acids is crosslinking of nucleic acids. For example, a crosslinking reaction of DNA or RNA blocks the intracellular flow of genetic information, and thus is used in the inhibition of gene expression. As a crosslinking agent for DNA, a compound called psoralen has been traditionally used as a photo-crosslinking agent (photo-crosslinking agent) that induces crosslinking through a photoreaction. A therapeutic method of internally taking psoralen, which is a photo-crosslinking agent, as a medicine, and carrying out photoirradiation, is in widespread use as one of standard therapeutic methods for psoriasis, which is a skin disease.

However, since the photo-crosslinking reaction of psoralen occurs preferentially with a 5'-TA-3' sequence between the two strands of nucleic acid, there is a problem that the target of the reaction that can be used is restricted. Furthermore, since the photocoupling wavelength for psoralen is 350 nm while its photocleavage wavelength is 250 nm, it is needed to use a short wavelength light source, in the case of using psoralen as a photo-crosslinking agent. Therefore, there is a problem that photoirradiation is likely to cause damages to DNA or cells.

Patent Document 1: Japanese Patent No. 3753938
Patent Document 2: Japanese Patent No. 3753942

DISCLOSURE OF THE INVENTION

Problem to be Solved by the Invention

Because of the problems as described above, there has been a demand for a photoreactive crosslinking agent that can be used for those sequences which cannot be photo-crosslinked by psoralen. There has also been a demand for a photoreactive crosslinking agent that is capable of photo-crosslinking using a light having a longer wavelength, as compared with psoralen.

Therefore, it is an object of the present invention to provide a photoreactive crosslinking agent (a photoreactive crosslinker) that is capable of crosslinking a sequence which cannot be photo-crosslinked by psoralen. It is another object of the present invention to provide a photoreactive crosslinking agent capable of photo-crosslinking using a light having a longer wavelength, as compared with psoralen.

Means for Solving the Problem

The inventors of the present invention devotedly conducted search and investigation on photoreactive crosslinking agents, and as a result, the inventors found a novel photoreactive crosslinking agent (photoreactive crosslinker) compound that is capable of crosslinking a sequence which cannot be photo-crosslinked by psoralen. Thus, the inventors found that the objects described above can be achieved by using this photoreactive crosslinking agent compound.

When this photoreactive crosslinking agent compound is used, crosslinks induced by photoirradiation can be formed for those sequences which cannot be photo-crosslinked by psoralen, and this crosslink-forming reaction can be carried out using a light having a longer wavelength, as compared with psoralen.

The compound according to the present invention has a characteristic structure in which a vinyl group has been added to a carbazole structure, and exhibits photo-crosslinkability through this relatively small structure. Thus, the compound can be modified by various ways and can be used for various purposes, as in the case of psoralen. Furthermore, this characteristic structure of the compound according to the present invention has a structure similar to the base of nucleic acids, and therefore can be used as an artificial base (artificial nucleobase). That is, an artificial nucleoside and an artificial nucleotide can be produced by introducing the characteristic structure of the compound according to the present invention as an artificial base, and an artificial nucleic acid compound containing such an artificial nucleotide in the sequence can be produced. When such an artificial nucleic acid compound forms a crosslink by a photoreaction, this is led to photo-crosslinks formed (photo-crosslinking) from one of the strands of a double helix to the other strand. Thus, a photoreactive nucleic acid compound can be used as a photo-crosslinking agent for double helix, which is capable of specifically reacting with a desired sequence.

Therefore, the present invention provides the following items [1] to [9].

[1] A compound having a group represented by the following formula (I):

[Chemical Formula 1]

(I)

(wherein in the formula (I), Ra represents a cyano group, an amide group, a carboxyl group, a C2-C7 alkoxycarbonyl group, or hydrogen; and R1 and R2 each independently represent a cyano group, an amide group, a carboxyl group, a C2-C7 alkoxycarbonyl group, or hydrogen), coupled with a group represented by the following formula (II):

Rb—    Formula (II)

(wherein Rb represents hydrogen, a sugar (the sugar includes ribose and deoxyribose), a polysaccharide (the polysaccharide includes a polyribose chain and a polydeoxyribose chain of nucleic acids), a polyether, a polyol, a polypeptide chain (the polypeptide chain includes a polypeptide chain of peptide nucleic acids), or a water-soluble synthetic polymer).

[2] The compound according to [1], wherein Rb represents a group represented by the following formula (III) or formula (IV):

[Chemical Formula 2]

(III)

[Chemical Formula 3]

(IV)

or hydrogen.

[3] A photoreactive crosslinking agent containing the compound according to any one of [1] and [2].

[4] A nucleoside having a group represented by the formula (I) according to [1] (wherein in the formula (I), Ra represents a cyano group, an amide group, a carboxyl group, a C2-C7 alkoxycarbonyl group, or hydrogen; R1 and R2 each independently represent a cyano group, an amide group, a carboxyl group, a C2-C7 alkoxycarbonyl group, or hydrogen) as a base moiety.

[5] A photoreactive crosslinking agent containing the nucleoside according to [4].

[6] A nucleotide having a group represented by the formula (I) according to [1] (wherein in the formula (I), Ra represents a cyano group, an amide group, a carboxyl group, a C2-C7 alkoxycarbonyl group, or hydrogen; R1 and R2 each independently represent a cyano group, an amide group, a carboxyl group, a C2-C7 alkoxycarbonyl group, or hydrogen) as a base moiety.

[7] A photoreactive crosslinking agent containing the nucleotide according to [6].

[8] A nucleic acid compound (the nucleic acid compound includes a nucleic acid and a peptide nucleic acid) having a group represented by the formula (I) according to [1] (wherein in the formula (I), Ra represents a cyano group, an amide group, a carboxyl group, a C2-C7 alkoxycarbonyl group, or hydrogen; R1 and R2 each independently represent a cyano group, an amide group, a carboxyl group, a C2-C7 alkoxycarbonyl group, or hydrogen) as a base moiety.

[9] A photoreactive crosslinking agent containing the nucleic acid compound according to [8].

The present invention also provides the following items [10] to [13].

[10] A method for forming a photo-crosslink(s) (a photo-crosslinking(s)) using the compound according to anyone of [1] and [2], between the compound and a nucleobase having a pyrimidine ring.

[11] A method for forming a photo-crosslink(s) (a photo-crosslinking(s)) using the nucleoside according to [4], between the nucleoside and a nucleobase having a pyrimidine ring.

[12] A method for forming a photo-crosslink(s) (a photo-crosslinking(s)) using the nucleotide according to [6], between the nucleotide and a nucleobase having a pyrimidine ring.

[13] A method for forming a photo-crosslink(s) (a photo-crosslinking(s)), the method including the steps of:

hybridizing the nucleic acid compound according to [5] and another nucleic acid compound having a pyrimidine ring as a nucleobase to form a double helix; and irradiating the formed double helix with light.

Furthermore, the present invention also provides the following items [14] to [17].

[14] Use of the compound according to any one of [1] and [2], for forming a photo-crosslink(s) (a photo-crosslinking(s)) between the compound and a nucleobase having a pyrimidine ring.

[15] Use of the nucleoside according to [4], for forming a photo-crosslink(s) (a photo-crosslinking(s)) between the nucleoside and a nucleobase having a pyrimidine ring.

[16] Use of the nucleotide according to [6], for forming a photo-crosslink(s) (a photo-crosslinking(s)) between the nucleotide and a nucleobase having a pyrimidine ring.

[17] Use of the nucleic acid compound according to [5], for forming a photo-crosslink(s) (a photo-crosslinking(s)) between the nucleic acid compound and another nucleic acid compound having a pyrimidine ring as a nucleobase, in the double helix formed by hybridization.

Effect of the Invention

According to the present invention, a crosslink resulting from photoirradiation can be formed for sequences which cannot be photo-crosslinked by psoralen. That is, according to the present invention, crosslinking can be extensively carried out for the bases in a sequence that cannot be used with psoralen, of which the target of crosslinking is limited to 5'-TA-3' sequences.

Furthermore, the characteristic structure of the compound according to the present invention, in which a vinyl group has been added to a carbazole structure, can be used as an artificial nucleobase. When nucleic acid compounds which contain this artificial base and are included in a specific sequence, are hybridized with nucleic acid compounds in a sequence that is complementary to the foregoing sequence, and thereby form a double helix, a photo-crosslink can be formed (photo-crosslinking) for the base of a nucleic acid compound in the complementary sequence, which is located at a specific position in the sequence.

Therefore, according to the present invention, not only a photo-crosslink can be formed for the bases in various sequences which cannot be photo-crosslinked by psoralen, but also a photo-crosslink can be formed for the bases that are at specific positions in a certain specific sequence, by forming a complementary strand.

The crosslink-forming reaction according to the present invention can be carried out using a light having a longer wavelength, as compared with psoralen. Accordingly, it can be avoided to use a light source of short wavelength, and thus there is less concern for any damage to DNA or cells due to photoirradiation.

Furthermore, the crosslink-forming reaction according to the present invention can be carried out with photoirradiation of a very short duration, as compared with psoralen. That is, since crosslink formation is carried out rapidly, the reaction can be used also for the uses where rapidity of reaction is required. Moreover, even from the viewpoint of the time for photoirradiation being short, there is less concern for any damage to DNA or cells due to photoirradiation.

BEST MODES FOR CARRYING OUT THE INVENTION

Figure 1:
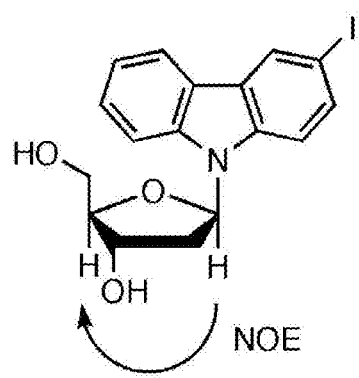
FIG. 1 is a diagram showing the NOESY spectrum of 3-iodocarbazole-1'-deoxyriboside.
Figure 1:
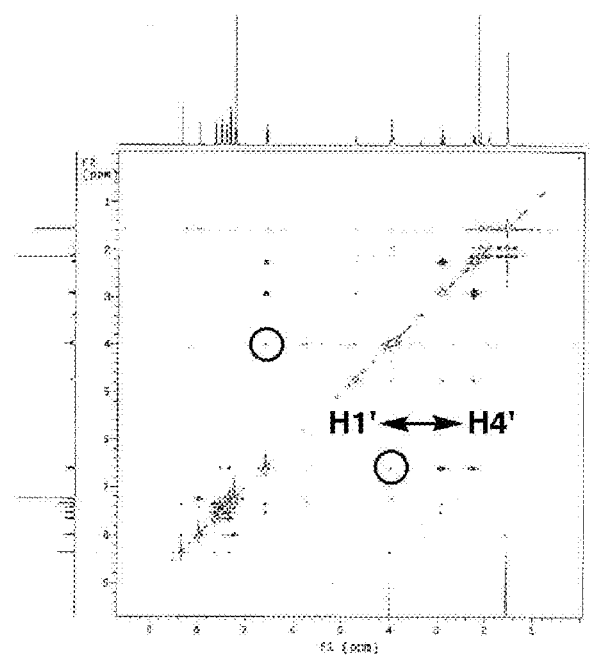

The present invention will be explained below in detail. The present invention is not intended to be limited to the following specific embodiments.

The present invention lies in a compound having a group represented by the following formula (I):

[Chemical Formula 4]

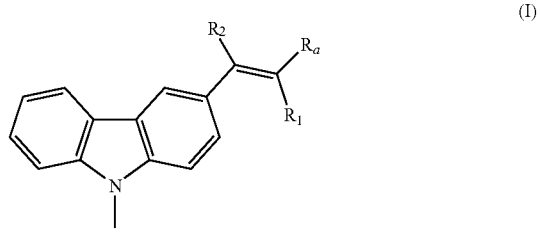

(I)

(wherein in the formula (I), Ra represents a cyano group, an amide group, a carboxyl group, a C2-C7 alkoxycarbonyl group, or hydrogen; and R1 and R2 each independently represent a cyano group, an amide group, a carboxyl group, a C2-C7 alkoxycarbonyl group, or hydrogen, coupled with a group represented by the following formula Rb—      Formula II (wherein Rb represents hydrogen, a sugar (the sugar includes ribose and deoxyribose), a polysaccharide (the polysaccharide includes a polyribose chain and a polydeoxyribose chain of nucleic acids), a polyether, a polyol, a polypeptide chain (the polypeptide chain includes a polypeptide chain of peptide nucleic acids), or a water-soluble synthetic polymer).

That is, the present invention lies in a compound represented by the following formula (V), in which the group represented by the formula (I) is coupled with the group represented by the formula (II):

[Chemical Formula 5]

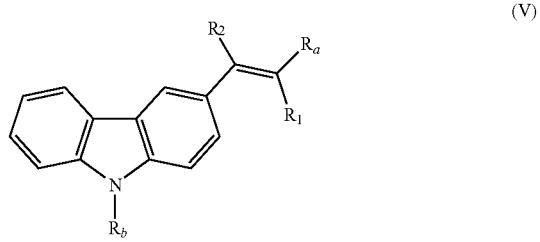

(V)

(wherein in the formula (V), Ra, R1, R2 and Rb have the same definitions as described for the formula (I) and formula (II)).

The above compound according to the present invention can form crosslinks by photoirradiation for a sequence that cannot be photo-crosslinked by psoralen, and can also induce a photo-crosslinking reaction using a light having a longer wavelength, as compared with psoralen.

Ra represents a cyano group, an amide group, a carboxyl group, an alkoxycarbonyl group, or hydrogen; preferably a cyano group, an amide group, a carboxyl group, an alkoxycarbonyl group, or hydrogen; and even more preferably a cyano group, an amide group, a carboxyl group, or an alkoxycarbonyl group. For the alkoxycarbonyl group, preferably a C2-C7 group, more preferably a C2-C6 group, even more preferably a C2-C5 group, even more preferably a C2-C4 group, even more preferably a C2-C3 group, and particularly preferably a C2 group can be used.

R1 and R2 each independently represent a cyano group, an amide group, a carboxyl group, an alkoxycarbonyl group, or hydrogen; preferably a cyano group, an amide group, a carboxyl group, an alkoxycarbonyl group, or hydrogen; and even more preferably a cyano group, an amide group, a carboxyl group, or an alkoxycarbonyl group. For the alkoxycarbonyl group, preferably a C2-C7 group, more preferably a C2-C6 group, even more preferably a C2-C5 group, even more preferably a C2-C4 group, even more preferably a C2-C3 group, and particularly preferably a C2 group can be used.

Rb represents hydrogen, a sugar (the sugar includes ribose and deoxyribose), a polysaccharide (the polysaccharide includes a polyribose chain and a polydeoxyribose chain of nucleic acids), a polyether, a polyol, a polypeptide chain (the polypeptide chain includes a polypeptide chain of peptide nucleic acids), or a water-soluble synthetic polymer.

According to a preferred embodiment, hydrogen can be used as Rb, and the compound according to the present invention in this case is represented by the following formula (VI):

[Chemical Formula 6]

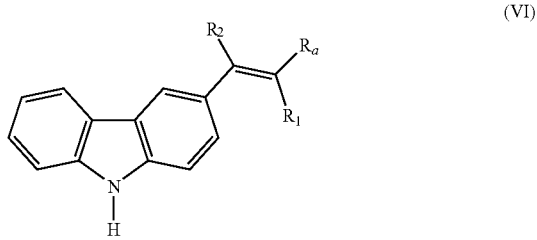

(VI)

(wherein in the formula (VI), Ra, R1 and R2 have the same definitions as described for the formula (I).

According to another preferred embodiment, ribose can be used as Rb, and an example of the compound according to the present invention in this case is a nucleoside (ribonucleoside) represented by the following formula (VII):

[Chemical Formula 7]

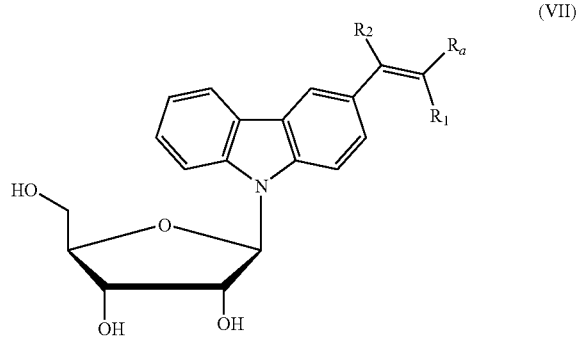

(VII)

(wherein in the formula (VII), Ra, R1 and R2 have the same definitions as described for the formula (I)).

According to another preferred embodiment, deoxyribose can be used as Rb, and an example of the compound according to the present invention in this case is a nucleoside (deoxyribonucleoside) represented by the following formula (VIII):

[Chemical Formula 8]

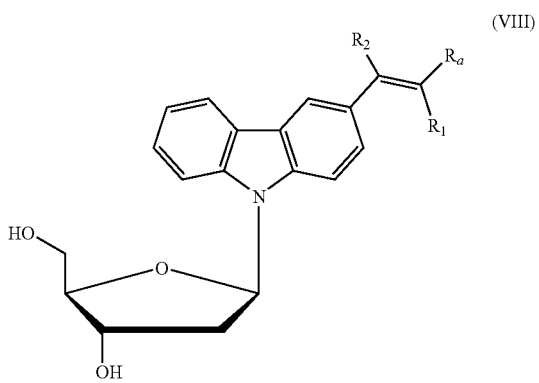

(VIII)

(wherein in the formula (VIII), Ra, R1 and R2 have the same definitions as described for the formula (I)).

The compound according to the present invention can be used as a nucleic acid compound (a photo-crosslinkable nucleic acid compound) having a characteristic structure in which a vinyl group has been added to a carbazole structure as a photoreactive artificial nucleobase. The nucleic acid compound can be hybridized with a sequence having a base sequence that is complementary to the nucleic acid compound, and can thereby form a double helix with the complementary chain. When the formed double helix is subjected to photoirradiation, the photoreactive artificial nucleobase forms a photo-crosslink with a base which is present in the complementary chain of the photo-crosslinkable nucleic acid compound. The base to be crosslinked to the photoreactive artificial nucleobase is the next base on the 3'-terminal side to a base which is located to a position suitable for base-pairing with the photoreactive artificial nucleobase.

The counterpart base with which the photoreactive artificial nucleobase according to the present invention can form a photo-crosslink, is a base having a pyrimidine ring. On the other hand, the photoreactive artificial nucleobase according to the present invention does not form a photo-crosslink with a base having a purine ring. That is, the photo-crosslinkable compound according to the present invention has a strong specificity such that the compound forms a photo-crosslink with cytosine, uracil and thymine among naturally occurring nucleobases, but does not form a photo-crosslink with guanine and adenine.

The photo-crosslinking agent (photo cross-linker) compound according to the present invention, when used as a nucleic acid compound having a photoreactive artificial nucleobase (i.e. photo-crosslinkable nucleic acid compound), can be hybridized with a sequence having a base sequence that is complementary to the nucleic acid compound, and can thereby form a double helix. Therefore, the photo-crosslinking agent compound can cause a photo-crosslinking reaction to be carried out only for an intended specific sequence (a target sequence). That is, the photo-crosslinking agent compound according to the present invention can impart a very high sequence-selectivity that is impossible with conventional photo-crosslinking agents such as psoralen, through designing of a sequence as desired.

Furthermore, when the photo-crosslinking agent compound according to the present invention is used as a nucleic acid compound having a photoreactive artificial nucleic acid base (a photo-crosslinkable nucleic acid compound), is hybridized with a sequence having a base sequence complementary to the nucleic acid compound to thereby form a double helix, the base which should form a base pair with the photoreactive artificial nucleobase according to the present invention in the complementary chain of photo-crosslinkable nucleic acid compounds, is not particularly limited, and can be freely selected.

The nucleic acid compound according to the present invention includes a nucleic acid and a peptide nucleic acid (PNA), and also includes a mononucleotide. The nucleic acid includes DNA and RNA, which are natural nucleic acids, and also includes modified nucleic acids such as LNA (BNA), which are non-natural (artificial) nucleic acids.

The light that is irradiated for photo-crosslinking is preferably a light having a wavelength in the range of generally 350 to 380 nm, more preferably in the range of 360 to 370 nm, and even more preferably 366 nm. The light is particularly preferably a laser light having a single wavelength of 366 nm.

The photo-crosslinking agent compound according to the present invention can further undergo photocleavage by photoirradiation, after being photo-crosslinked with another nucleic acid (nucleic acid compound) by photoirradiation. That is, the photo-crosslinking agent compound according to the present invention enables reversible photo-crosslinking, and thus can be used as a reversible photo-crosslinking agent.

Regarding the light that is irradiated for photocleavage, a light having a wavelength in the range of generally 330 to 370 nm, and preferably in the range of 330 to 360 nm, can be used. Furthermore, according to a preferred embodiment, a light having a wavelength of 366 nm, and particularly preferably a laser light having a single wavelength of 366 nm, can be used.

According to a preferred embodiment, the photoreactions according to the present invention involving photo-crosslinking and photocleavage can be carried out by irradiation with a light having a wavelength in the range of 350 to 370 nm, and preferably, the photoreactions can be carried out using a laser light having a single wavelength of 366 nm. When a light having a wavelength in this range is used, both of the photoreactions such as photo-crosslinking and photocleavage can be carried out by means of a same light source, and thus it is advantageous in that there is no need to provide two types of light sources. In the case of using alight having a wavelength in this range, control of which photoreaction between photo-crosslinking and photocleavage would proceed, can be achieved by the temperature conditions. In order to make a photo-crosslinking reaction to proceed, photoirradiation is carried out at a temperature in the range of generally 0 to 50° C., preferably 0 to 40° C., more preferably 0 to 30° C., even more preferably 0 to 20° C., even more preferably 0 to 10° C., and even more preferably 0 to 5° C., and particularly preferably at 0° C. In order to make a photocleavage reaction to proceed, photoirradiation is carried out at a temperature in the range of generally 60 to 100° C., preferably 60 to 90° C., and more preferably 70 to 90° C.

Since the photo-crosslinking and photocleavage according to the present invention utilize photoreactions, there is no particular limitation on the pH, temperature, salt concentration or the like, and the reactions can be carried out by photoirradiation in a solution set at a pH, a temperature and a salt concentration, at which biopolymers such as nucleic acid compounds can stably exist.

The photo-crosslinking and photocleavage according to the present invention proceed very rapidly, and for example, the photoreaction proceeds for only one second (under irradiation with a light at 366 nm) under the conditions at which psoralen would require several hours (under irradiation with a light at 350 nm). That is, when the photo-crosslinking agent according to the present invention is used, photo-crosslinks can be formed by carrying out the photoreaction by photoirradiation for a time period of several seconds, for example, for 1 to 9 seconds, for 1 to 7 seconds, for 1 to 5 seconds, or for 1 to 3 seconds.

EXAMPLES

The present invention will be described below by way of Examples. The present invention is not intended to be limited to the following Examples.

[1. Synthesis of ODN Having Vinylcarbazole at Base Site]

Synthesis was carried out according to the following Scheme 1. In the explanation given below, the compounds may be occasionally represented by the numbers attached to the compounds.

Scheme 1

[Chemical Formula 9]

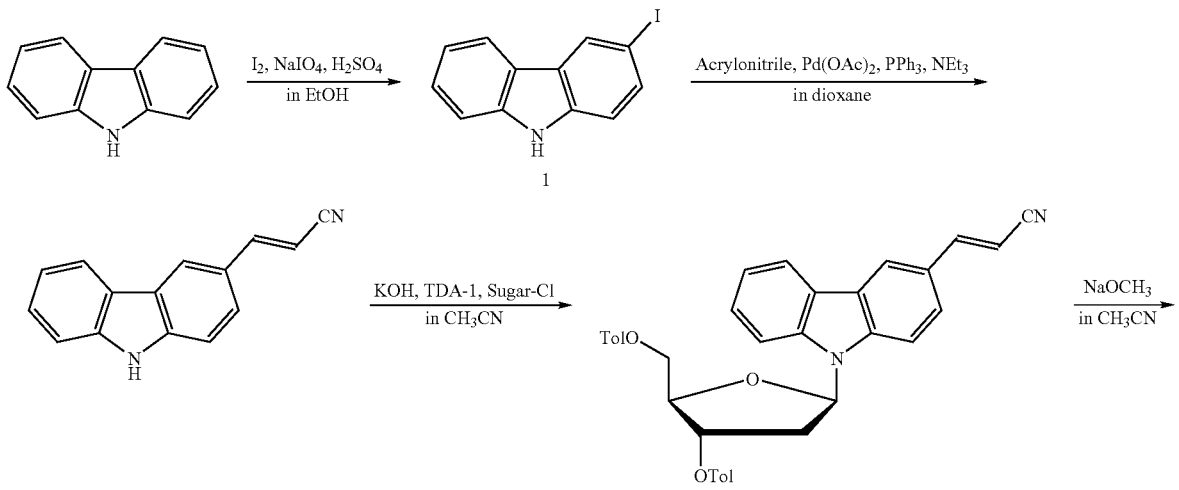

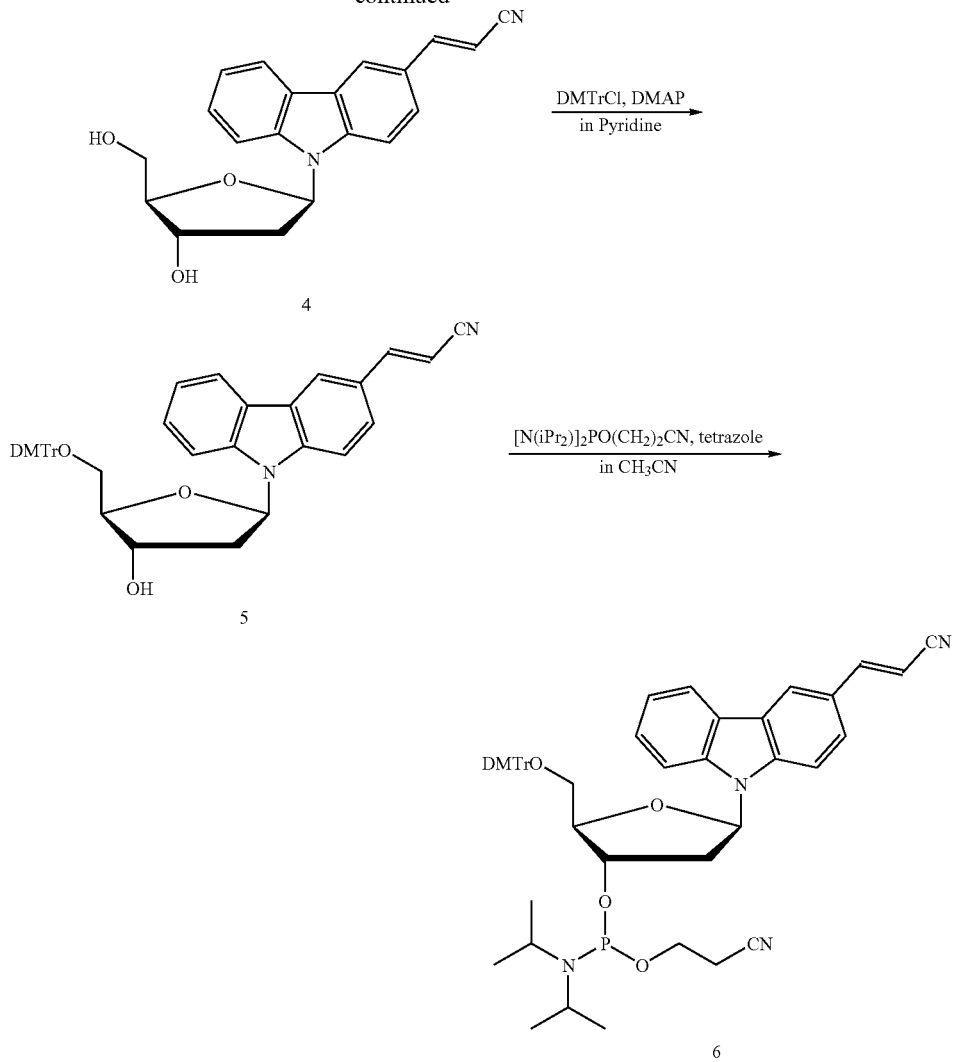

3-Iodocarbazole (1)

To an ethanol solution (500 mL) of carbazole (2.50 g, 15.0 mmol), $NaIO_4$ (0.80 g, 3.75 mmol) and $I_2$ (1.89 g, 7.45 mmol) were added in this order, and then an ethanol solution (100 mL) of $H_2SO_4$ (1.60 mL, 30.0 mmol) was added thereto. The reaction solution was heated to reflux for one hour at 65° C. Disappearance of the raw materials was confirmed by TLC (HexH:AcOEt=4:1), and an ethanol solution (100 mL) of NaOH (1.4 g) was added thereto to neutralize the reaction solution. Ethanol was removed, and then the reaction solution was extracted two times with chloroform and washed two times with water. The organic phase was dried over $Na_2SO_4$, and the solvent was removed. The residue was purified by column chromatography (HexH:AcOEt=4:1), and compound (1) (3.06 g, 70%) was obtained as a white powder. Thus, 3,6-diiodocarbazole (0.47 g, 7.5%) was obtained as a white powder.

1: $^1$H NMR (DMSO-$d_6$) δ 11.4 (s, 1H), 8.49 (d, 1H, J=1.7 Hz), 8.14 (d, 1H, J=8.0 Hz), 7.62 (dd, 1H, J=8.4, 1.7 Hz), 7.48 (d, 1H, J=8.0 Hz), 7.40 (m, 1H), 7.33 (d, 2H, J=8.4 Hz), 7.16 (m, 1H).

3,6-Diiodocarbazole: $^1$H NMR (DMSO-$d_6$) δ 11.5 (s, 1H), 8.56 (d, 2H, J=1.7 Hz), 7.65 (dd, 2H, J=8.5, 1.7 Hz), 7.34 (d, 2H, J=8.5 Hz).

3-Cyanovinylcarbazole (2)

To a dioxane solution (10 mL) of triphenylphosphine (139 mg, 0.53 μmol), palladium acetate (40.0 mg, 0.18 μmol) and triethylamine (0.59 μL, 4.23 mmol) were added in this order. The mixture was stirred for 5 minutes at 75° C. A dioxane solution (15 mL) of the compound (1) (1.03 g, 3.52 mmol) and acrylonitrile (0.46 μL, 7.04 mmol) were added thereto, and the reaction solution was heated to reflux for 11.5 hours. Generation of a product was confirmed by TLC (HexH:AcOEt=4:1), and then palladium powder was removed by cotton filtration. The residue was purified by column chromatography (HexH:AcOEt=4:1), and compound (2) (0.14 g, 18%, trans:cis=97:3) was obtained as a white powder. Thus, compound (1) (0.37 g, recovery rate 37%) was recovered as a white powder.

2: $^1$H NMR (DMSO-$d_6$) δ 11.6 (s, 1H), 8.44 (s, 1H), 8.11 (d, 1H, J=8.0 Hz), 7.75 (d, 1H, J=16.7 Hz), 7.69-7.72 (m, 1H), 7.40-7.52 (m, 3H), 7.19-7.24 (m, 1H), 6.36 (d, 1H, J=16.7 Hz).

3-Cyanovinylcarbazole-1'-β-deoxyriboside-3',5'-di-(p-toluoyl) ester (3)

To an acetonitrile solution (20 mL) of KOH (0.22 g, 3.87 mmol) and TDA-1 (11 mg, 34 µmol), compound (2) (0.26 g, 1.20 mmol) was added at room temperature. The mixture was stirred for 20 minutes. Chlorosugar (0.53 g, 1.24 mmol) was added to the reaction solution, and the resulting mixture was stirred for 20 minutes at room temperature. Disappearance of the raw materials was confirmed by TLC (HexH:AcOEt=4:1). Precipitates were removed, and then the reaction solution was purified by column chromatography (CHCl$_3$). Thus, compound (3) (0.23 g, 33%) was obtained as a yellow oil.

3: $^1$H NMR (CDCl$_3$) δ 8.09 (s, 1H), 8.02 (d, 2H, J=8.4 Hz), 7.98 (d, 2H, J=8.4 Hz), 7.62-7.65 (m, 1H), 7.62 (d, 1H, J=8.8 Hz), 7.49 (d, 1H, J=16.5 Hz), 7.25-7.31 (m, 7H), 7.17-7.20 (m, 1H), 6.68 (dd, 1H, J=9.3, 5.8 Hz), 5.78 (m, 1H), 5.76 (d, 1H, J=16.5 Hz), 4.91 (dd, 1H, J=12.4, 2.7 Hz), 4.78 (dd, 1H, J=12.4, 3.3 Hz), 4.55-4.57 (m, 1H), 3.09-3.20 (m, 1H), 2.45-2.52 (m, 1H), 2.45 (s, 3H), 2.44 (s, 3H), HRMS (MALDI): calcd. for C$_{36}$H$_{30}$N$_2$O$_5$Na [(M+Na)]$^+$593.2053, found 593.2018.

3-Cyanovinylcarbazole-1'-β-deoxyriboside (4)

To a methanol solution (20 mL) of compound (3) (0.22 g, 0.39 mmol), 0.5 M methanolic NaOMe (2.3 mL, 1.2 mmol) and chloroform (5.0 mL) were added, and the reaction solution was stirred for 3.5 hours at room temperature. Disappearance of the raw materials was confirmed by TLC (CHCl$_3$:MeOH=9:1). The solvent was removed, and then the residue was purified by column chromatography (CHCl$_3$:MeOH=9:1). Thus, compound (4) (0.11 g, 81%) was obtained as a white powder.

4: $^1$H NMR (CDCl$_3$) δ 8.12 (d, 1H, J=1.7 Hz), 8.06 (d, 1H, J=7.7 Hz), 7.59 (d, 1H, J=9.1 Hz), 7.43-7.57 (m, 4H), 7.26-7.31 (m, 1H), 6.64 (dd, 1H, J=8.2, 6.9 Hz), 5.87 (d, 1H, J=16.5 Hz), 4.77-4.82 (m, 1H), 3.95-4.06 (m, 3H), 2.95 (dt, 1H, J=14.0, 8.2 Hz), 2.30 (ddd, 1H, J=14.0, 6.9, 3.3 Hz), HRMS (MALDI): calcd. for C$_{20}$H$_{18}$N$_2$O$_3$Na [(M+Na)]$^-$357.1215, found 357.1265.

5'-O-(4,4'-dimethoxytrityl)-3-cyanovinylcarbazole-1'-β-deoxyriboside (5)

Pyridine (0.5 mL) was added to compound (4) (97 mg, 0.29 mmol), which had been azeotropically boiled with pyridine (1.0 mL×2). To the reaction solution, a pyridine solution (1.0 mL) of 4,4'-dimethoxytrityl chloride (118 mg, 0.35 mmol) and 4-(dimethylamino)pyridine (7.0 mg, 58 µmol) was added, and the reaction solution was stirred for 18 hours at room temperature. Generation of a product was confirmed by TLC (CHCl$_3$:MeOH=95:5), and then pyridine was removed. The residue was purified by column chromatography (CHCl$_3$:MeOH=98:2), and thus compound (5) (113 mg, 61%) was obtained as a yellow powder.

5: $^1$H NMR (CDCl$_3$) δ 8.07 (d, 1H, J=1.7 Hz), 8.02-8.05 (m, 1H), 7.71 (d, 1H, J=8.5 Hz), 7.62-7.65 (m, 1H), 7.45-7.52 (m, 3H), 7.33-7.37 (m, 4H), 7.25-7.28 (m, 4H), 7.12 (dd, 1H, J=8.8, 1.7 Hz), 6.81 (dd, 4H, J=8.8, 1.7 Hz), 6.61 (dd, 1H, J=8.2, 6.3 Hz), 5.77 (d, 1H, J=16.7 Hz), 4.80-4.82 (m, 1H), 4.05-4.07 (m, 1H), 3.77 (s, 3H), 3.76 (s, 3H), 3.56-3.58 (m, 2H), 2.89 (dt, 1H, J=13.8, 8.2 Hz), 2.23 (ddd, 1H, J=13.8, 6.3, 2.7 Hz), 1.98 (d, 1H, J=3.6 Hz), HRMS (MALDI): calcd. for C$_{41}$H$_{36}$N$_2$O$_5$Na [(M+Na)]$^-$659.2522, found 659.2485.

5'-O-(4,4'-dimethoxytrityl)-3-cyanovinylcarbazole-1'-β-deoxyriboside-3'-O-(cyanoethoxy-N,N-diisopropylamino)phosphoramidite (6)

Acetonitrile (1.5 mL) was added to compound (5) (0.11 g, 0.17 mol), which had been azeotropically boiled with acetonitrile (1.5 mL). To the reaction solution, 2-cyanoethyl-N,N,N',N'-tetraisopropylphosphorodiamidite (52 µL, 0.17 mol) and an acetonitrile solution (0.37 mL, 0.17 mol) of 0.45 M tetrazole was added, and the reaction solution was stirred for 1.0 hour at room temperature. The reaction solution was extracted two times with deacetation-treated ethyl acetate, and the residue was washed with a saturated aqueous solution of NaHCO$_3$ and H$_2$O. The organic phase was dried over MgSO$_4$, and the solvent was removed. Compound (6) (0.12 g), which was a crude product in the form of yellow oil, was transferred in acetonitrile to a rubber-sealed bottle, and was azeotropically boiled three times. The resultant was used in DNA synthesis without further purification.

[Synthesis of ODN Containing 3-Cyanovinylcarbazole-1'-β-Deoxyriboside ($^{CNV}$K)]

ODNs containing $^{CNV}$K as shown below were synthesized.
ODN(A$^{CNV}$K): 5'-TGCA$^{CNV}$KCCGT-3'
ODN(G$^{CNV}$K): 5'-TGCG$^{CNV}$KCCGT-3'
ODN(C$^{CNV}$K): 5'-TGCC$^{CNV}$KCCGT-3'
ODN(T$^{CNV}$K): 5'-TGCT$^{CNV}$KCCGT-3'

[Chemical Formula 10]

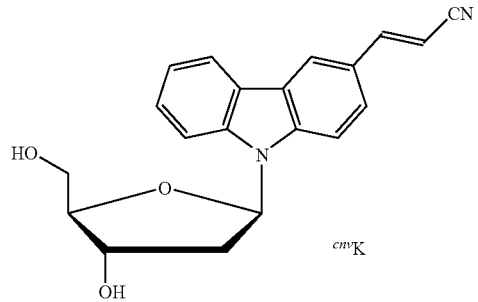

Synthesis was carried out according to the following Scheme 2.

Scheme 2

[Chemical Formula 11]

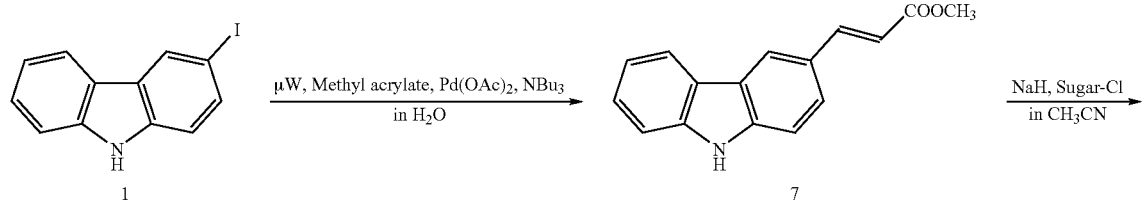

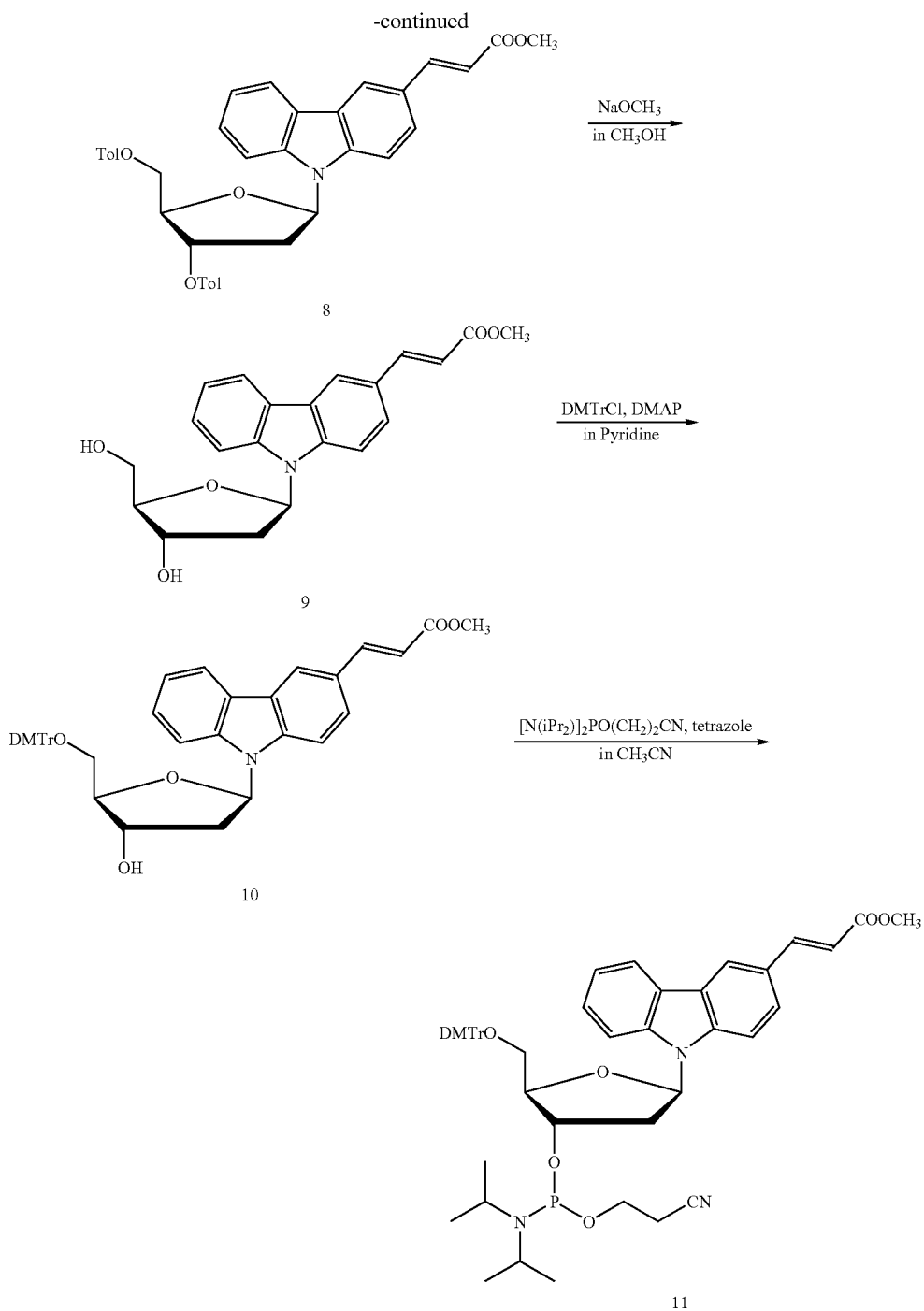

3-Methoxycarbonylvinylcarbazole (7)

To a DMF solution (0.25 mL) of palladium acetate (38.0 mg, 0.17 μmol), compound (1) (0.50 g, 1.71 mmol) as well as tributylamine (0.41 μL, 1.71 mmol), methyl acrylate (0.38 L, 4.27 mmol) and $H_2O$ (1.0 mL) were added in this order. The reaction solution was allowed to react for 10 minutes at 160° C. using microwaves, and the reaction was traced by TLC to confirm the disappearance of compound (1). The palladium powder was removed by Kiriyama filtration, and then the residue was purified by column chromatography (HexH:A-cOEt=3:1). Thus, compound (7) (0.26 g, 62%) was obtained as a white powder.

7: $^1$H NMR ($CDCl_3$) δ 8.26 (s, 1H), 8.21 (s, 1H), 8.07 (d, 1H, J=8.0 Hz), 7.89 (d, 1H, J=15.9 Hz), 7.61 (dd, 1H, J=1.7, 8.5 Hz), 7.39-7.44 (m, 3H), 7.23-7.29 (m, 1H), 6.47 (d, 1H, J=15.9 Hz), 3.81 (s, 3H).

3-Methoxycarbonylcarbazole-1'-β-deoxyriboside-3', 5'-di-(p-toluoyl)ester (8)

To an acetonitrile solution (49 mL) of compound (7) (0.55 g, 2.22 mmol), NaH (92.0 mg, 2.31 mmol) was added at room temperature, and the mixture was stirred for 10 minutes. Chlorosugar (1.14 g, 2.66 mmol) was added to the reaction solution, and the resulting mixture was stirred for 60 minutes at room temperature. Disappearance of the raw materials was confirmed by TLC (HexH:AcOEt=4:1). Precipitates were removed, and then the residue was purified by column chromatography (HexH:AcOEt=4:1). Thus, compound (8) (0.98 g, 71%) was obtained as a white powder.

3-Methoxycarbonylcarbazole-1'-β-deoxyriboside (9)

To a methanol solution (46 mL) of compound (8) (0.96 g, 1.59 mmol), 0.5 M methanolic NaOMe (9.6 mL, 4.8 mmol) and dichloromethane (12 mL) were added, and the reaction solution was stirred for one hour at room temperature. Disappearance of the raw materials was confirmed by TLC (CHCl$_3$:MeOH=9:1). The solvent was removed, and then the residue was purified by column chromatography (CHCl$_3$:MeOH=9:1). Thus, compound (9) (0.28 g, 48%) was obtained as a white powder.

9: $^1$H NMR (CDCl$_3$) δ 8.20 (s, 1H), 8.06 (d, 1H, J=7.7 Hz), 7.86 (d, 1H, J=15.9 Hz), 7.53-7.61 (m, 3H), 7.44 (t, 1H, J=7.1 Hz), 7.24-7.27 (m, 1H), 6.63 (dd, 1H, J=8.2, 7.0 Hz), 6.46 (d, 1H, J=15.9 Hz), 4.75-4.80 (m, 1H), 3.95-4.04 (m, 3H), 3.81 (s, 1H), 2.95 (dt, 1H, J=14.0, 8.2 Hz), 2.28 (ddd, 1H, J=14.0, 7.0, 3.6 Hz).

5'-O-(4,4'-dimethoxytrityl)-3-methoxycarbonylvinyl-carbazole-1'-β-deoxyriboside (10)

Pyridine (0.5 mL) was added to compound (9) (0.23 g, 0.63 mmol), which had been azeotropically boiled with pyridine (1.0 mL×2). To the reaction solution, a pyridine solution (2.2 mL) of 4,4'-dimethoxytrityl chloride (0.26 g, 0.75 mmol) and 4-(dimethylamino)pyridine (15.0 mg, 0.13 μmol) was added, and the reaction solution was stirred for 16 hours at room temperature. Generation of a product was confirmed by TLC (CHCl$_3$:MeOH=95:5), and then pyridine was removed. The residue was purified by column chromatography (CHCl$_3$:MeOH=99:1), and thus compound (10) (0.21 g, 51%) was obtained as a yellow powder.

10: $^1$H NMR (CDCl$_3$) δ 8.17 (s, 1H), 8.02-8.05 (m, 1H), 7.83 (d, 1H, J=15.9 Hz), 7.62-7.66 (m, 3H), 7.46-7.49 (m, 2H), 7.34-7.38 (m, 4H), 7.25-7.28 (m, 4H), 7.15 (d, 1H, J=8.8 Hz), 6.81 (dd, 4H, J=8.8, 1.4 Hz), 6.61 (dd, 1H, J=8.5, 6.3 Hz), 6.40 (d, 1H, J=15.9 Hz), 4.76-4.80 (m, 1H), 4.05-4.09 (m, 1H), 3.80 (s, 3H), 3.77 (s, 3H), 3.76 (s, 3H), 3.56-3.57 (m, 2H), 2.89 (dt, 1H, J=14.0, 8.5 Hz), 2.18 (m, 1H), 2.17 (d, 1H, J=3.8 Hz).

5'-O-(4,4'-dimethoxytrityl)-3-methoxycarbonylvinyl-carbazole-1'-β-deoxyriboside-3'-O-(cyanoethoxy-N,N-diisopropylamino)phosphoramidite (11)

Acetonitrile (1.3 mL) was added to compound (10) (0.20 g, 0.29 μmol), which had been azeotropically boiled with acetonitrile (1.0 mL). To the reaction solution, 2-cyanoethyl-N,N,N',N'-tetraisopropylphosphorodiamidite (92 μL, 0.29 μmol) and an acetonitrile solution (0.65 mL, 0.29 μmol) of 0.45 M tetrazole was added, and the reaction solution was stirred for 2 hours at room temperature. The reaction solution was extracted two times with deacetation-treated ethyl acetate, and the residue was washed with a saturated aqueous solution of NaHCO$_3$ and H$_2$O. The organic phase was dried over MgSO$_4$, and the solvent was removed. Compound (11) (0.25 g), which was a crude product in the form of yellow oil, was transferred in acetonitrile to a rubber-sealed bottle, and was azeotropically boiled three times. The resultant was used in DNA synthesis without further purification.

[Synthesis of Modified ODN]

ODN(AX) (5'-TGCAXCCGT-3', X=9) and ODN(GX) (5'-TGCGXCCGT-3', X=9) were synthesized using an ABI 3400 DNA synthesizer. The CPG of each of the obtained reaction mixtures was divided into two portions, and one portion of the reaction mixture was deprotected by incubating the mixture at 37° C. for 17 hours using 0.4M NaOH in H$_2$O:CH$_3$OH=1:4, and was subjected to neutralization with 2 M TEAA, followed by freeze-drying. The other portion of the reaction mixture was deprotected by incubating the mixture at room temperature for 17 hours using 0.05 M K$_2$CO$_3$ in CH$_3$OH, and was subjected to neutralization with 2 M TEAA, followed by freeze-drying. The DNAs of ODN(A$^{OHV}$K), ODN(G$^{OHV}$K), ODN(A$^{OMeV}$K) and ODN(G$^{OMeV}$K) were purified by reverse phase HPLC. Each of the DNAs was enzymatically degraded. The isolation yields were 5, 10, 11 and 13%, respectively. The molecular weights were measured by MALDI-TOF-MS.

calcd. for ODN(A$^{OHV}$K), 5'-TGCA$^{OHV}$KCCGT-3': [(M+H)$^+$] 2801.93, found 2802.12.

calcd. for ODN(G$^{OHV}$K), 5'-TGCG$^{OHV}$KCCGT-3': [(M+H)$^+$] 2817.93, found 2818.08.

calcd. for ODN(A$^{OMeV}$K), 5'-TGCA$^{OMeV}$KCCGT-3': [(M+H)$^+$] 2815.95, found 2816.07.

calcd. for ODN(G$^{OMeV}$K), 5'-TGCG$^{OMeV}$KCCGT-3': [(M+H)$^+$] 2831.95, found 2831.98.

ODNs containing $^{NH2V}$K as shown below were synthesized.

ODN(A$^{NH2V}$K): 5-TGCA$^{NH2V}$KCCGT-3
ODN(G$^{NH2V}$K): 5-TGCG$^{NH2V}$KCCGT-3

[Chemical Formula 12]

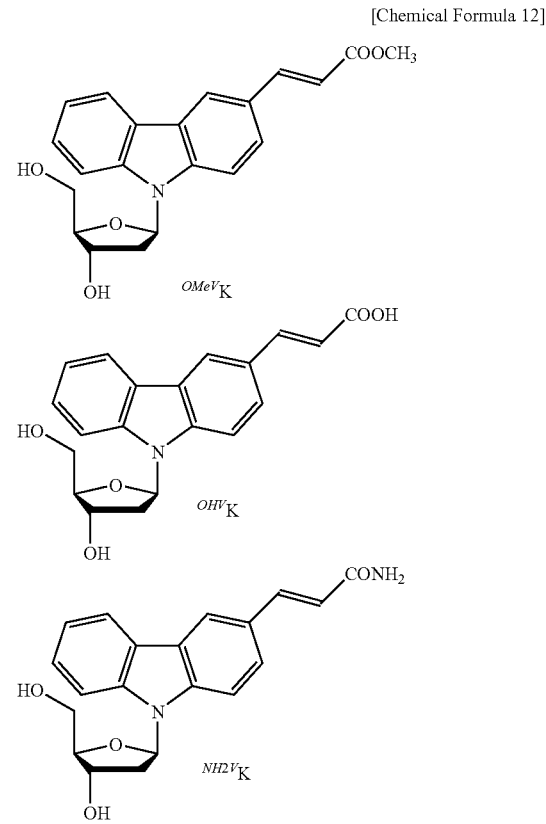

[2. Measurement of NOESY Spectrum of Nucleoside Having Vinylcarbazole at Base Site]

A NOESY spectrum of 3-iodocarbazole-1'-deoxyriboside was measured. In the NOESY spectrum, cross peaks were seen between H1' and H4' (FIG. 1). 3-Iodocarbazole-1'-deoxyriboside is believed to be a β-form.

[3. Photo-Crosslinking Reaction Using ODNs Containing $^{CNV}$K]

Figure 2:
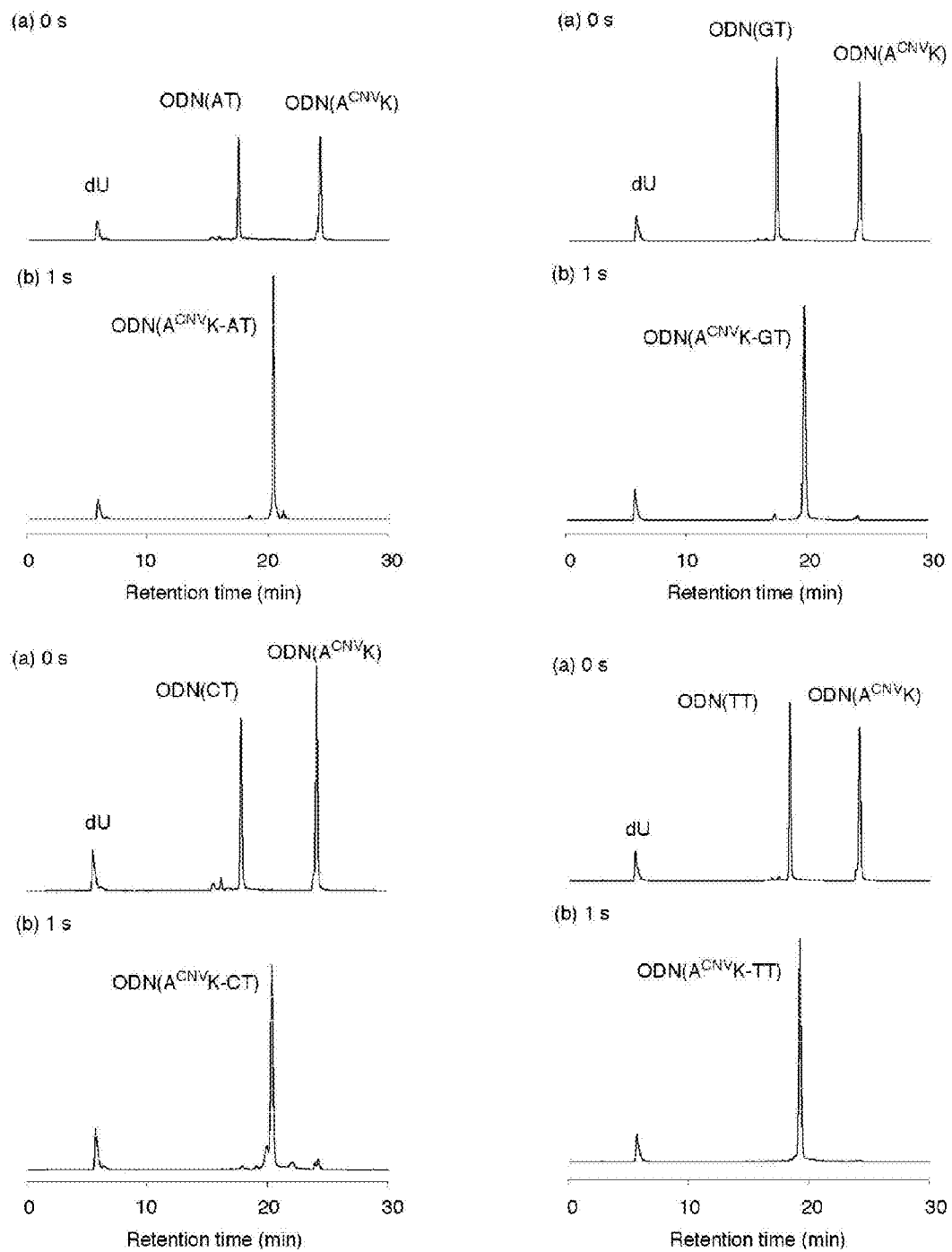
FIG. 2 is a set of chromatograms showing the results of an HPLC analysis of a photo-crosslinking reaction experiment for ODN(XT) and ODN($A^{CNV}K$)

Photo-crosslinking reactions were carried out using ODNs containing $^{CNV}$K (see the following Scheme 3). Photo-crosslinking reactions of ODN(A$^{CNV}$K) (20 µM) and ODN (XT) (20 µM, X=A, G, C and T) were carried out (50 mM sodium cacodylate, 100 mM NaCl, total volume: 30 µL). A light at 366 nm was irradiated using a UV-LED for one second at 0° C. The results of an HPLC analysis of the resulting photoreaction products are presented in FIG. 2 (elution with a solvent mixture of 50 mM ammonium formate, pH 7.0; linear gradient over 30 min from 3% to 20% acetonitrile). Photoirradiation of ODN(A$^{CNV}$K) was carried out in the presence of ODN(XT). FIG. 2(a) presents the results of an HPLC analysis before irradiation, and FIG. 2(b) presents the results of the HPLC analysis obtained after irradiation with a light at 366 nm for one second.

Scheme 3

[Chemical Formula 13]

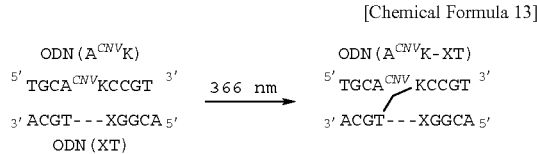

Figure 3:
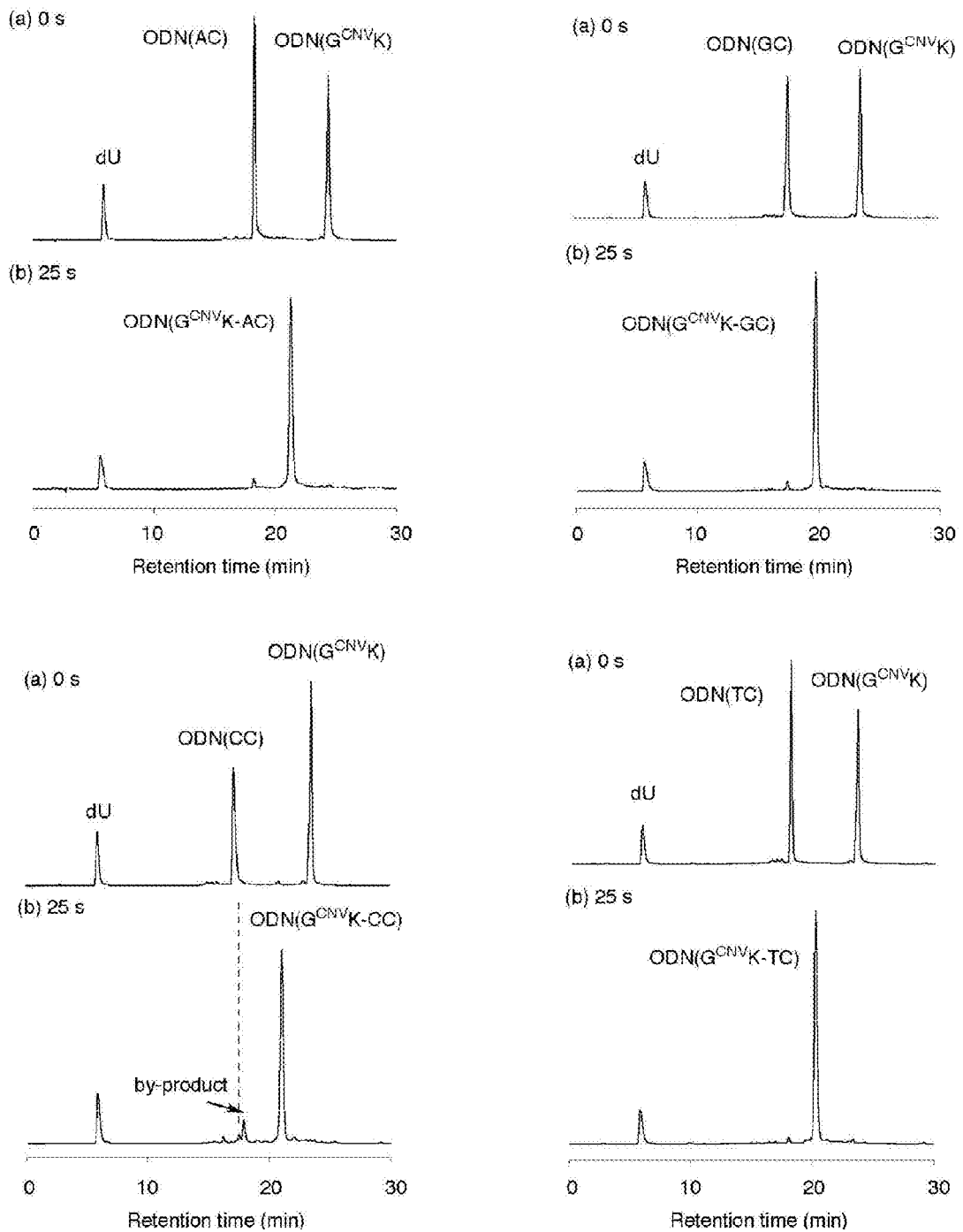
FIG. 3 is a set of chromatograms showing the results of an HPLC analysis of a photo-crosslinking reaction experiment for ODN(XC) and ODN($G^{CNV}K$)

Similarly, a photo-crosslinking reaction was carried out using ODNs containing $^{CNV}$K, in which C serves as a photo-crosslinking site (see the following Scheme 4). Photo-crosslinking reactions of ODN(G$^{CNV}$K) (20 µM) and ODN (XC) (20 µM, X=A, G, C and T) were carried out (50 mM sodium cacodylate, 100 mM NaCl, total volume: 30 µL). A light at 366 nm was irradiated using a UV-LED for 25 seconds at 0° C. The results of an HPLC analysis of the resulting photoreaction products are presented in FIG. 3. Photoirradiation of ODN(G$^{CNV}$K) was carried out in the presence of ODN(XC). FIG. 3(a) presents the results of an HPLC analysis before irradiation, and FIG. 3(b) presents the results of the HPLC analysis obtained after irradiation with a light at 366 nm for 25 seconds.

Scheme 4

[Chemical Formula 14]

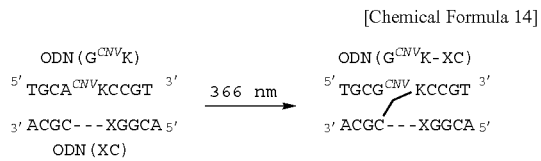

Figure 4:
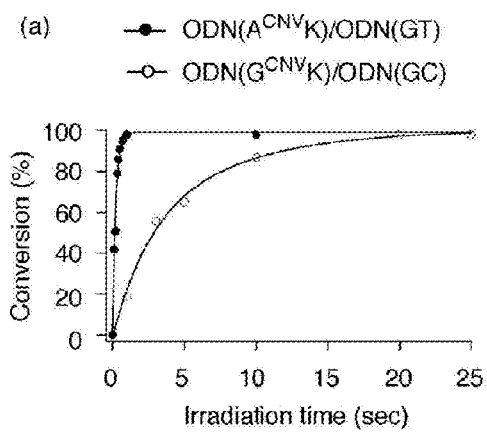
FIG. 4 is a graph comparing the rates of a photo-crosslink (photo-crosslinking) reaction between ODN($A^{CNV}K$) and ODN($G^{CNV}K$)
Figure 4:
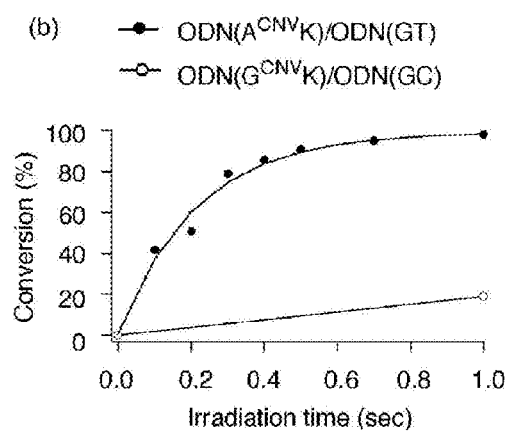

In the photo-crosslinking reaction using ODNs containing $^{CNV}$K, the photo-crosslinking reaction proceeded sufficiently regardless of whether the photo-crosslinking site was T or C (FIG. 4). FIG. 4 is a graph comparing the rates of photo-crosslink (photo-crosslinking) reactions of ODN(A$^{CNV}$K) (closed circles) and ODN(G$^{CNV}$K) (open circles).

[4. Sixteen Kinds of Photo-Crosslinking Reactions Using ODNs Containing $^{CNV}$K]

Figure 5:
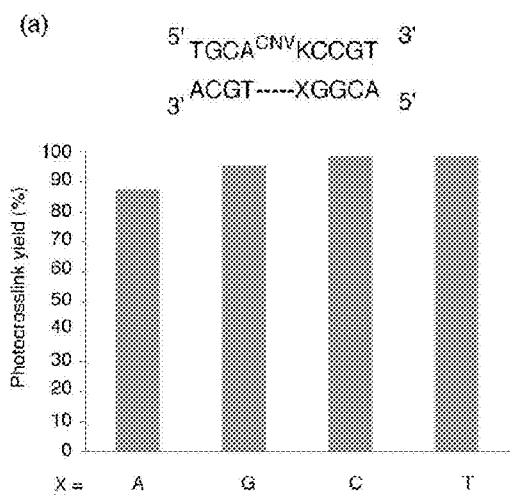
FIG. 5 is a set of diagrams showing the experiment results for examining the sequence-specificity of ODNs containing $^{CNV}K$.
Figure 5:
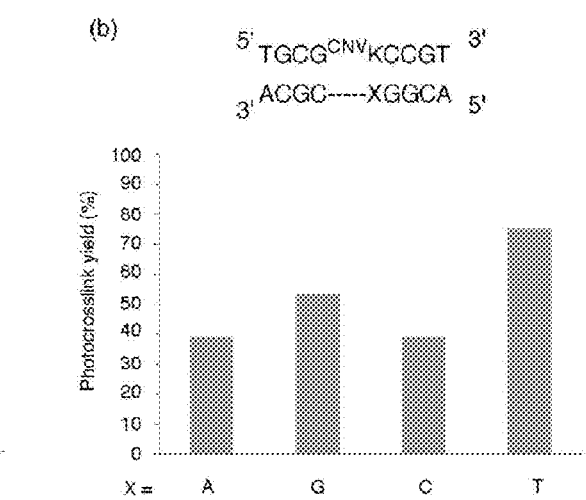
Figure 5:
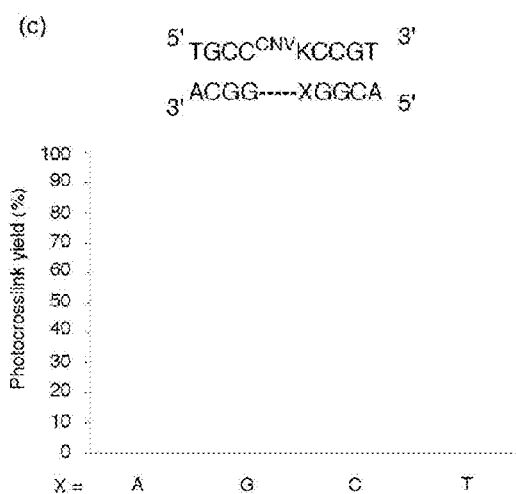
Figure 5:
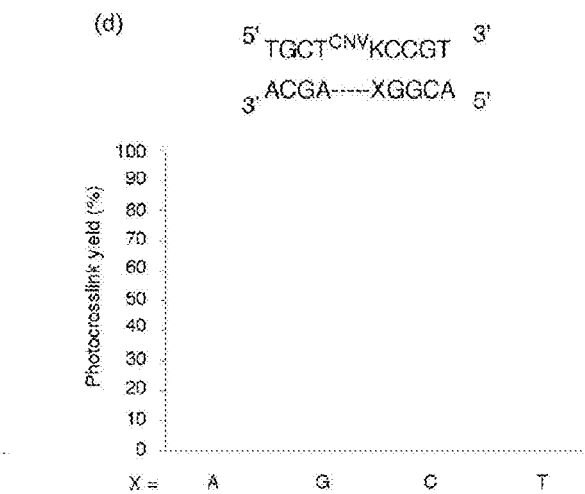

Sixteen kinds of photo-crosslinking reactions were carried out using ODNs containing $^{CNV}$K. Photo-crosslinking reactions of ODN(A$^{CNV}$K), ODN(G$^{CNV}$K), ODN(C$^{CNV}$K) and ODN(T$^{CNV}$K) (10 µM) as well as ODN(XT), ODN(XC), ODN(XG) and ODN(XA) (X=A, G, C and T, 10 µM) were carried out (50 mM sodium cacodylate, 100 mM NaCl, total volume: 200 µL). A light at 366 nm was irradiated using a UV-LED for one second at 0° C., and an analysis was made using HPLC (elution with a solvent mixture of 50 mM ammonium formate, pH 7.0; linear gradient over 3.4 min from 2% to 15% acetonitrile, column temperature 30° C.). The results are presented in FIG. 5.

Sixteen kinds of photo-crosslinking reactions were carried out, and as a result, the following was discovered.

The photo-crosslinking reactions proceed efficiently when the target of crosslinking is T and C. Particularly, if the target of crosslinking is T, the reaction proceeds quantitatively in one second. On the other hand, if the target of crosslinking is A or G, the reaction does not proceed.

[5. Photo-Crosslinking Reaction Using ODNs Containing $^{OMeV}$K or $^{OHV}$K]

Figure 6:
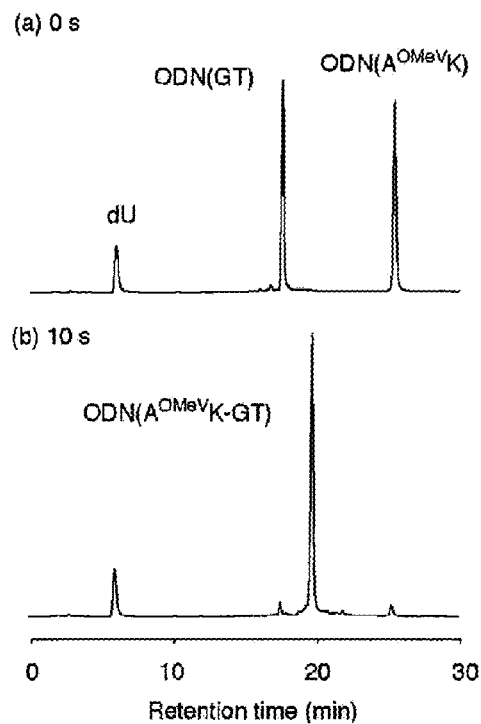
FIG. 6 is a set of chromatograms showing the results of an HPLC analysis of a photo-crosslinking reaction experiment for ODN ($A^{OMeV}K$) and ODN(GT)

Photo-crosslinking reactions were carried out using ODNs containing $^{OMeV}$K. Photo-crosslinking reactions of ODN (A$^{OMeV}$K) (20 µM) and ODN(GT) (20 µM) were carried out (50 mM sodium cacodylate, 100 mM NaCl, total volume: 105 µL). A light at 366 nm was irradiated using a UV-LED for 0.5, 1, 2, 3, 5, 10 and 20 seconds, respectively, at 0° C. (see the following Scheme 5). The results of an HPLC analysis of the photoreaction products are presented in FIG. 6 (elution with a solvent mixture of 50 mM ammonium formate, pH 7.0; linear gradient over 30 min from 3% to 20% acetonitrile).

Scheme 5

[Chemical Formula 15]

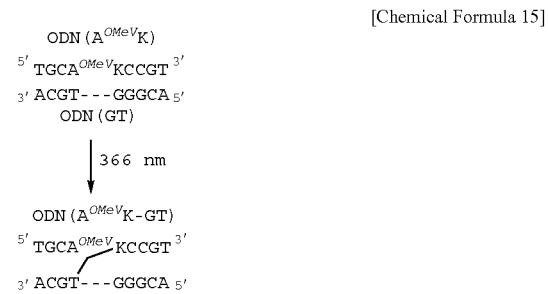

Figure 7:
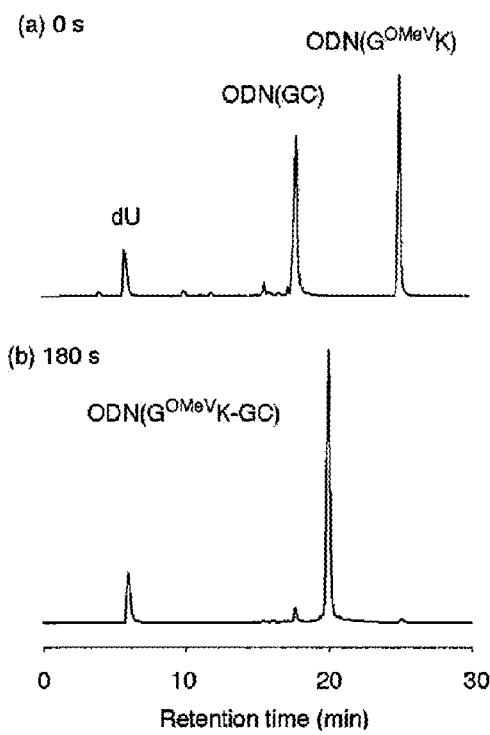
FIG. 7 is a set of chromatograms showing the results of an HPLC analysis of a photo-crosslinking reaction experiment for ODN($G^{OMeV}K$) and ODN(GC)

Similarly, photo-crosslinking reactions were carried out using ODNs containing $^{OMeV}$K in which C serves as a photo-crosslinking site. Photo-crosslinking reactions of ODN(G$^{OMeV}$K) (20 µM) and ODN(GC) (20 µM) were carried out (50 mM sodium cacodylate, 100 mM NaCl, total volume: 30 µL). A light at 366 nm was irradiated using a UV-LED for 180 seconds at 0° C. (Scheme 6). The results of an HPLC analysis of the resulting photoreaction products are presented in FIG. 7.

Scheme 6

[Chemical Formula 16]

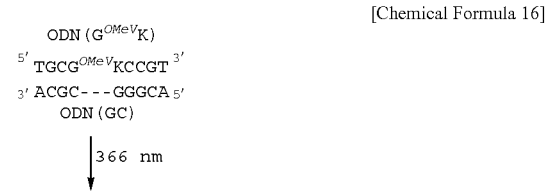

-continued

ODN($G^{OMeV}$K-GC)

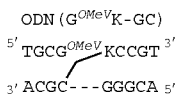

Figure 8:
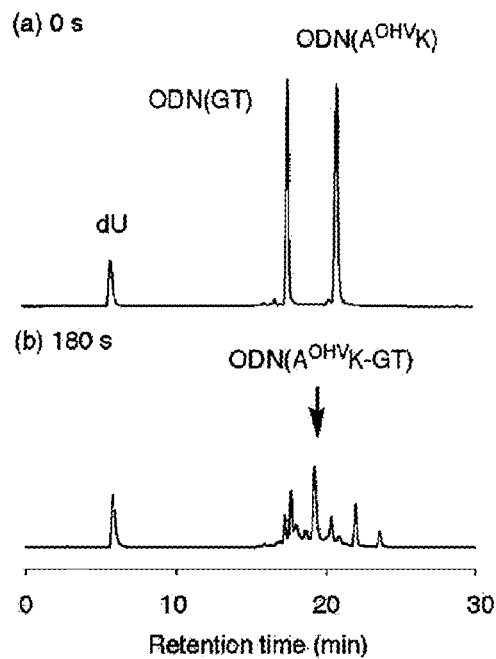
FIG. 8 is a set of chromatograms showing the results of an HPLC analysis of a photo-crosslinking reaction experiment for ODN($A^{OHV}K$) and ODN(GT)

Photo-crosslinking reactions were carried out using ODNs containing $^{OHV}$K. Photo-crosslinking reactions of ODN($A^{OHV}$K) (20 μM) and ODN(GT) (20 μM) were carried out (50 mM sodium cacodylate, 100 mM NaCl, total volume: 30 μL). A light at 366 nm was irradiated using a UV-LED for 1, 10, 25, 40, 60, 120 and 180 seconds, respectively, at 0° C. (see the following Scheme 7). The results of an HPLC analysis of the photoreaction products are presented in FIG. 8.

Scheme 7

[Chemical Formula 17]

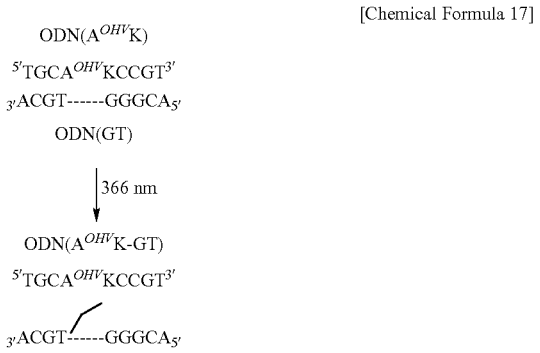

Figure 9:
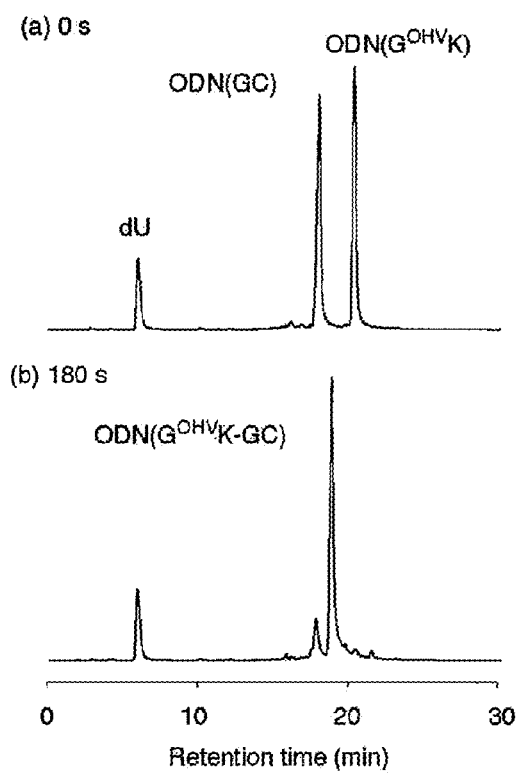
FIG. 9 is a set of chromatograms showing the results of an HPLC analysis of a photo-crosslinking reaction experiment for ODN($G^{OHV}K$) and ODN(GC)

Similarly, photo-crosslinking reactions were carried out using ODNs containing $^{OHV}$K, in which C serves as a photo-crosslinking site. Photo-crosslinking reactions of ODN($G^{OHV}$K) (20 μM) and ODN(GC) (20 μM) were carried out (50 mM sodium cacodylate, 100 mM NaCl, total volume: 30 μL). A light at 366 nm was irradiated using a UV-LED for 180 seconds at 0° C. (Scheme 8). The results of an HPLC analysis of the resulting photoreaction products are presented in FIG. 9.

Scheme 8

[Chemical Formula 18]

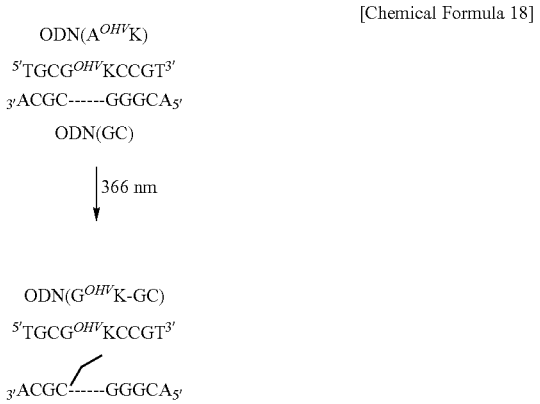

Figure 10:
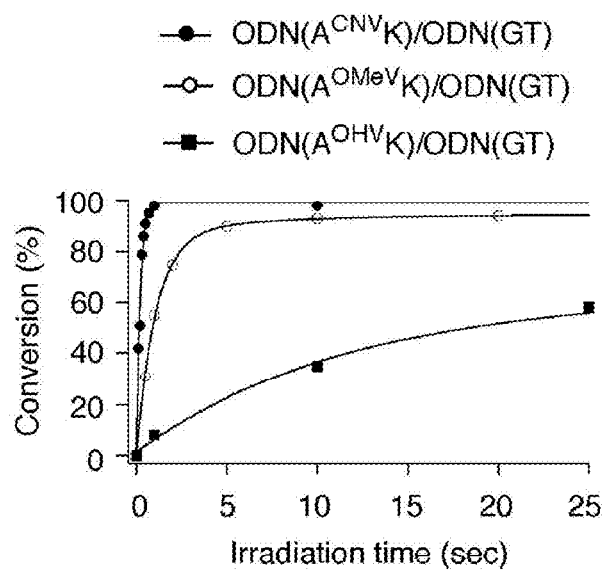
FIG. 10 is a graph comparing the rates of a photo-crosslinking reaction of ODN($A^{CNV}K$), ODN($A^{OMeV}K$) and ODN ($A^{OHV}K$)

In the photo-crosslinking reactions using ODNs containing $^{OMeV}$K, when the photo-crosslinking site was T, the photo-crosslinking reaction was completed in 10 seconds. When the photo-crosslinking site was C, the photo-crosslinking reaction was completed in 180 seconds. On the other hand, in the photo-crosslinking reactions using ODN containing $^{OHV}$K, when the photo-crosslinking site was T, the photo-crosslinking reaction was completed in 180 seconds, with a yield of 75%. When the photo-crosslinking site was C, the photo-crosslinking reaction was completed in 180 seconds. A comparison of changes over time of $^{CNV}$K and $^{OMeV}$K shows significant differences (FIG. 10). FIG. 10 is a graph comparing the rates of photo-crosslinking reactions of ODN($A^{CNV}$K) (closed circles), ODN($A^{OMeV}$K) (open circles) and ODN($A^{OHV}$K) (closed squares).

[6. Photocleavage Reaction of Photo-Crosslinked Body]

Figure 11:
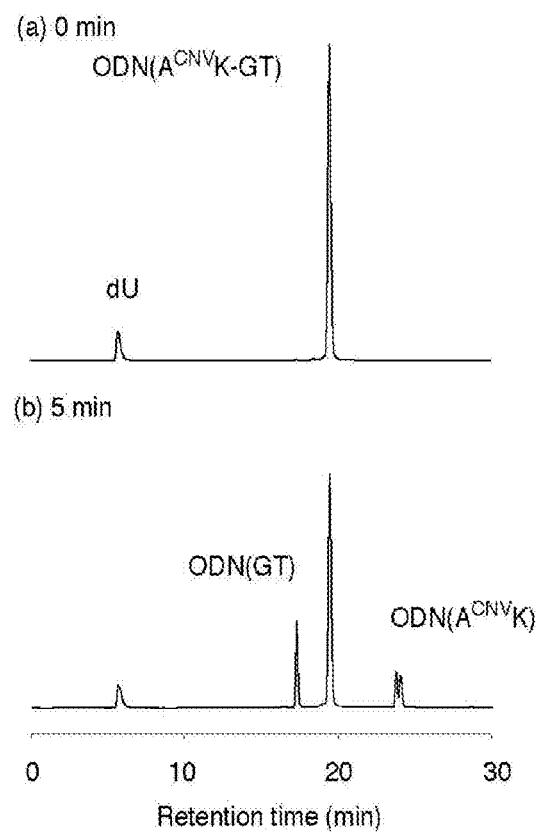
FIG. 11 is a set of chromatograms showing the results of photoirradiation and HPLC analysis of ODN($A^{CNV}K$-GT)

A photo-crosslinked body, ODN($A^{CNV}$K-GT) or ODN($G^{CNV}$K-GC), in which the photo-crosslinking site was T or C, was prepared by a photoreaction and was preparatively isolated by HPLC. Then, a photo-crosslinking reaction of ODN($A^{CNV}$K-GT) (20 μM) was carried out (50 mM sodium cacodylate, 100 mM NaCl, total volume: 30 μL). A light at 366 nm was irradiated using a transilluminator for 5 minutes at 70° C. (see the following Scheme 9). The results of an HPLC analysis of the photoreaction product are presented in FIG. 11. FIG. 11 shows the results of photoirradiating ODN($A^{CNV}$K-GT) at 0° C. and analyzing the resultant by HPLC, and FIG. 11(*a*) presents the results obtained before irradiation, while FIG. 11(*b*) presents the results obtained after irradiation with a light at 366 nm for 5 minutes.

Scheme 9

[Chemical Formula 19]

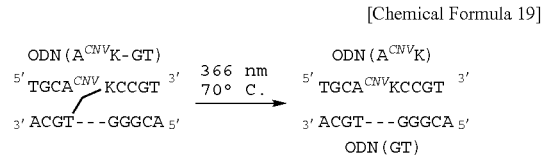

Figure 12:
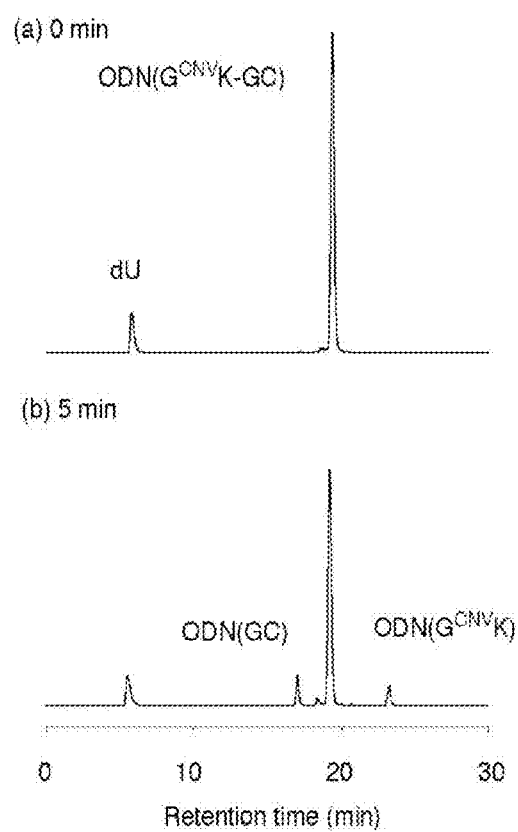
FIG. 12 is a set of chromatograms showing the results of photoirradiation and HPLC analysis of ODN($G^{CNV}K$-GC).

Similarly, a photo-crosslinking reaction of ODN($G^{CNV}$K-GC) was carried out (50 mM sodium cacodylate, 100 mM NaCl, total volume: 30 μL). A light at 366 nm was irradiated using a transilluminator for 5 minutes at 70° C. (see the following Scheme 10). The results of an HPLC analysis of the photoreaction product are presented in FIG. 12. The photocleavage reaction proceeded with a yield of 29 and 28%, respectively, when the photo-crosslinking site was T or C. In a photo-crosslinking reaction using ODNs containing $^{CNV}$K, photo-reversible reactivity was observed by changing the reaction temperature. FIG. 12 shows the results of photoirradiating ODN($G^{CNV}$K-GC) at 70° C. and analyzing the resultant by HPLC, and FIG. 12(*a*) presents the results obtained before irradiation, while FIG. 12(*b*) presents the results obtained after irradiation with a light at 366 nm for 5 minutes.

Scheme 10

[Chemical Formula 20]

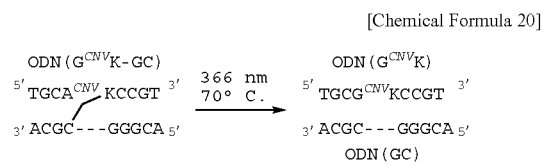

The invention claimed is:

1. An agent comprising:
a compound represented by the following formula (V)

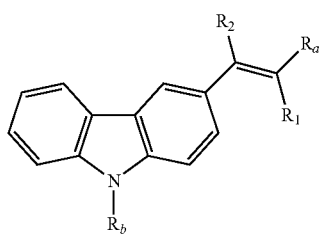
(V)

wherein, in the formula (V), $R_a$ represents a cyano group, an amide group, a carboxyl group, a C2-C7 alkoxycarbonyl group, or hydrogen, wherein, in the formula (V), $R_1$ and $R_2$ each independently represent a cyano group, an amide group, a carboxyl group, a C2-C7 alkoxycarbonyl group, or hydrogen, and wherein, in the formula (V), $R_b$ represents a sugar, a polysaccharide, a polyether, a polyol, a polypeptide chain, or a water-soluble synthetic polymer.

2. The agent according to claim 1,
wherein $R_b$ is represented by the following formula (III) or formula (IV):

[Chemical Formula 22]

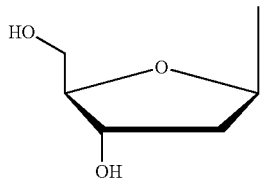
(III)

[Chemical Formula 23]

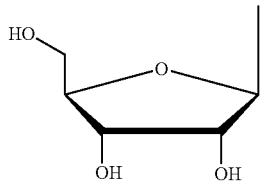
(IV)

3. The agent according to claim 1, wherein the compound is a nucleoside.

4. The agent according to claim 1, wherein the compound is a nucleotide.

5. The agent according to claim 1, wherein the compound is a nucleic acid.

6. The agent according to claim 1,
wherein $R_b$ is represented by the following formula (IX) or formula (X):

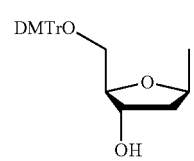
(IX)

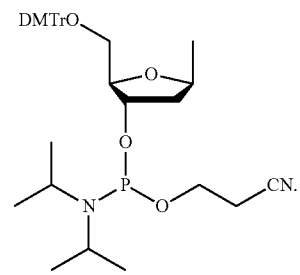
(X)

7. The agent according to claim 6,
wherein the compound is represented by one of the following formulae:

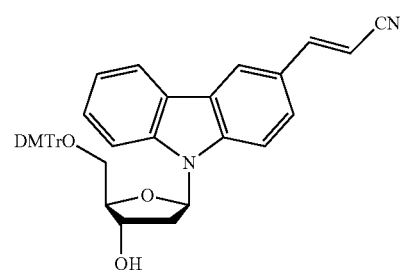

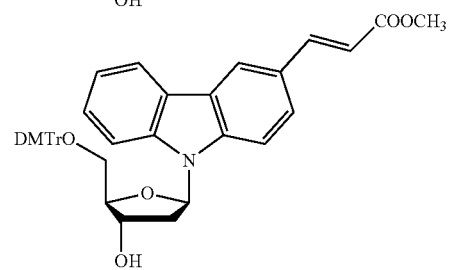

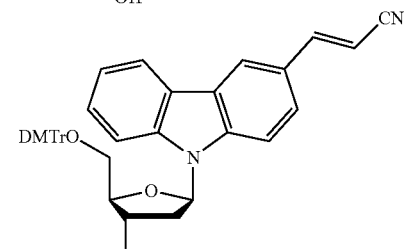

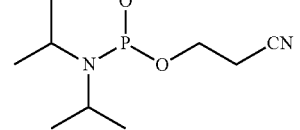

-continued

8. A method of forming a crosslink, comprising:
providing a compound and a nucleobase having a pyrimidine ring, and
irradiating the compound and the nucleobase with light,
wherein the compound is represented by the following formula (V):

wherein, in the formula (V), $R_a$ represents a cyano group, an amide group, a carboxyl group, a C2-C7 alkoxycarbonyl group, or hydrogen,
wherein, in the formula (V), $R_1$ and $R_2$ each independently represent a cyano group, an amide group, a carboxyl group, a C2-C7 alkoxycarbonyl group, or hydrogen, and
wherein, in the formula (V), $R_b$ represents a sugar, a polysaccharide, a polyether, a polyol, a polypeptide chain, or a water-soluble synthetic polymer.

9. The method of claim 8,
wherein $R_b$ is represented by the following formula (III) or formula (IV):

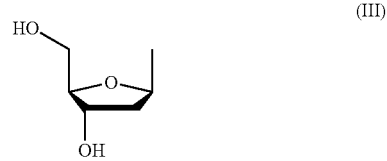

(III)

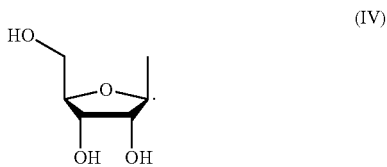

(IV)

10. A method for producing a nucleic acid, comprising:
synthesizing a nucleic acid using the compound of claim 6 as a synthesizing reagent.

11. A method for producing a nucleic acid, comprising:
synthesizing a nucleic acid using the compound of claim 7 as a synthesizing reagent.

* * * * *